US 11,744,844 B2

(12) United States Patent
Cassidy et al.

(10) Patent No.: US 11,744,844 B2
(45) Date of Patent: Sep. 5, 2023

(54) SELECTIVE ESTROGEN RECEPTOR DEGRADERS

(71) Applicant: Eli Lilly and Company, Indianapolis, IN (US)

(72) Inventors: Kenneth Charles Cassidy, Westfield, IN (US); Kishore Kumar Katyayan, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 17/691,713

(22) Filed: Mar. 10, 2022

(65) Prior Publication Data

US 2022/0296624 A1  Sep. 22, 2022

Related U.S. Application Data

(60) Provisional application No. 63/161,531, filed on Mar. 16, 2021.

(51) Int. Cl.
| | |
|---|---|
| *C07H 17/00* | (2006.01) |
| *C07D 491/052* | (2006.01) |
| *A61P 35/00* | (2006.01) |
| *A61K 31/706* | (2006.01) |
| *A61K 31/4741* | (2006.01) |

(52) U.S. Cl.
CPC ........ *A61K 31/706* (2013.01); *A61K 31/4741* (2013.01); *A61P 35/00* (2018.01); *C07D 491/052* (2013.01); *C07H 17/00* (2013.01)

(58) Field of Classification Search
None
See application file for complete search history.

(56) References Cited

FOREIGN PATENT DOCUMENTS

| WO | 2020/014435 A1 | 1/2020 | | |
|---|---|---|---|---|
| WO | WO-2020014435 A1 * | 1/2020 | ........... | A61K 31/436 |

OTHER PUBLICATIONS

Ervin, Samantha M., Joshua B. Simpson, Morgan E. Gibbs, Benjamin C. Creekmore, Lauren Lim, William G. Walton, Raad Z. Gharaibeh, and Matthew R. Redinbo. "Structural insights into endobiotic reactivation by human gut microbiome-encoded sulfatases." *Biochemistry* 59, No. 40 (2020): 3939-3950.

Ervin, Samantha M., Hao Li, Lauren Lim, Lee R. Roberts, Xue Liang, Sridhar Mani, and Matthew R. Redinbo. "Gut microbial β-glucuronidases reactivate estrogens as components of the estrobolome that reactivate estrogens." *Journal of Biological Chemistry* 294, No. 49 (2019): 18586-18599.

International Search Report and Written Opinion in International Application No. PCT/US2022/019770, dated Jul. 15, 2022, 14 pages.

Zhu, Bao Ting, and Allan H. Conney. "Functional role of estrogen metabolism in target cells: review and perspectives." *Carcinogenesis* 19, No. 1 (1998): 1-27.

* cited by examiner

*Primary Examiner* — Traviss C McIntosh, III
(74) *Attorney, Agent, or Firm* — Bradley W Crawford

(57) ABSTRACT

Novel selective estrogen receptor degraders (SERDs) according to the formula:

and pharmaceutically acceptable salt thereof and pharmaceutical compositions thereof, wherein R is selected from and .

21 Claims, No Drawings

SELECTIVE ESTROGEN RECEPTOR DEGRADERS

BACKGROUND

Selective estrogen receptor degraders (SERDs) bind to the estrogen receptor (ER) and downregulate ER-mediated transcriptional activity. This degradation and downregulation caused by SERDs can be useful in the treatment of cell proliferation disorders, such as cancer. Some small molecule examples of SERDs have been disclosed in the literature (see, e.g., WO2005073204, WO20144205136, and WO2016097071). However, known SERDs have not yet been as useful as is needed to effectively treat cancer. For example, finding SERDs with better pharmacokinetic (PK) and pharmacodynamic (PD) properties, higher efficiency in the clinic, and good oral bioavailability would be very helpful in treating cancer. A highly selective, antagonist SERD with inhibition of ER-mediated transcription would be expressly beneficial in treating cancer. There is a need for new SERDs to treat cancers such as breast cancer, ovarian cancer, endometrial cancer, prostate cancer, uterine cancer, gastric cancer, and lung cancer as well as mutations due to emerging resistance. In particular there is a need for new SERDs to treat ER-positive breast cancer, gastric cancer, and/or lung cancer.

Novel tetracyclic compounds and pharmaceutical salts thereof that act as SERDs are disclosed herein. The newly invented SERDs that are described herein provide inhibition of ER-mediated transcription that will be useful in treating cancers such as breast cancer, ovarian cancer, endometrial cancer, prostate cancer, uterine cancer, gastric cancer, and lung cancer as well as mutations due to emerging resistance. These SERDs can be used either as single agents or in combination with other classes of drugs including selective estrogen receptor modulators (SERMs), aromatase inhibitors, CDK4 inhibitors, CDK6 inhibitors, PI3K inhibitors, and mTOR inhibitors to treat hormone receptor-positive cancers such as breast cancer, gastric cancer, and/or lung cancer.

The novel compounds described herein are represented by Formula I:

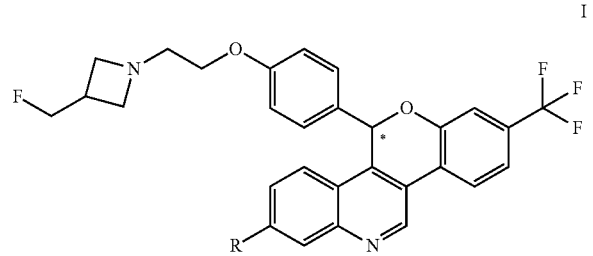

I wherein R is selected from

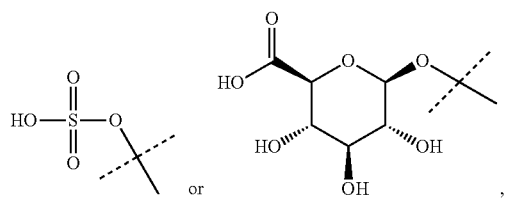

or a pharmaceutically acceptable salt thereof.

One of skill in the art will appreciate that compounds as described by Formula I, or pharmaceutically acceptable salts thereof, contain a chiral center, the position of which is indicated by *. One of skill in the art will also appreciate that the Cahn-Ingold-Prelog (R) or (S) designations for chiral centers will vary depending upon the substitution patterns around a chiral center. The chiral center in the compound of Formula I provides an R-enantiomeric form shown by Formula II:

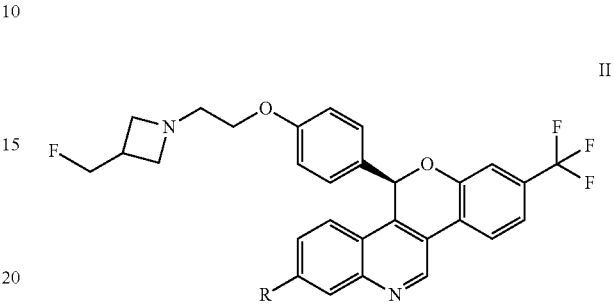

II

And an S-enantiomeric form shown by Formula III:

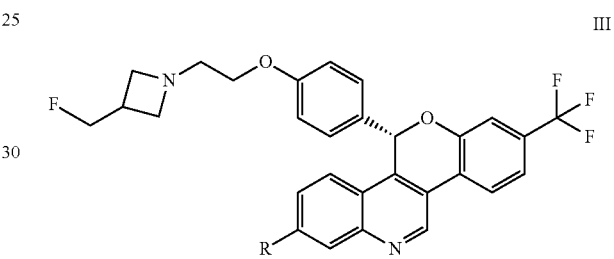

III

All individual stereoisomers, enantiomers, and diastereomers, as well as mixtures of the enantiomers and diastereomers of the compounds according to Formula I, Formula II, and Formula III including racemates are included within the scope of the compounds described herein. Compounds for pharmaceutical use that contain chiral centers are often isolated as single enantiomers or diastereomers and such isolated compounds of Formula I, Formula II, and Formula III are included within the scope of the compounds disclosed herein. One of skill in the art will also appreciate that the compounds of Formula I, Formula II, and Formula III described herein, and pharmaceutically acceptable salts thereof, can be deuterated (where a hydrogen can be replaced by a deuterium) and such molecules are considered to be included within the scope of the compounds disclosed herein.

Specific examples of the compounds of Formula I (including IUPAC nomenclature names) are shown here:

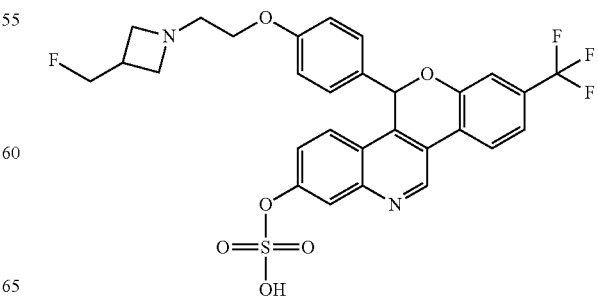

[5-[4-[2-[3-(fluoromethyl)azetidin-1-yl]ethoxy]phenyl]-8-(trifluoromethyl)-5H-chromeno[4,3-c]quinolin-2-yl] hydrogen sulfate;

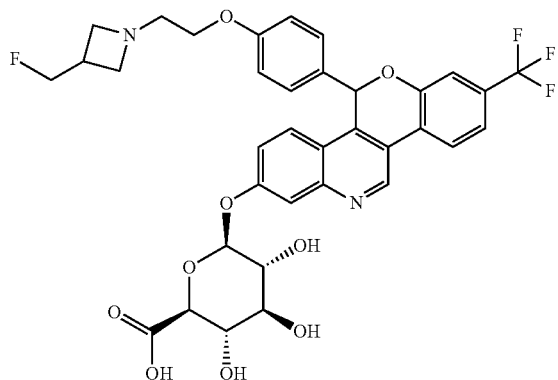 [SMILES: O=C(O)[C@H]1O[C@@H](Oc2ccc3c4c(cnc3c2)-c2ccc(C(F)(F)F)cc2OC4c2ccc(OCCN3CC(CF)C3)cc2)[C@H](O)[C@@H](O)[C@@H]1O]

(2S,3S,4S,5R,6S)-6-[[5-[4-[2-[3-(fluoromethyl)azetidin-1-yl]ethoxy]phenyl]-8-(trifluoromethyl)-5H-chromeno[4,3-c] quinolin-2-yl]oxy]-3,4,5-trihydroxy-tetrahydropyran-2-carboxylic acid;

Due to the chiral center of Formula I indicated by *, each of these specific examples of compounds of Formula I shown above have R- and S-enantiomeric forms (i.e., R-enantiomeric compounds of Formula II and S-enantiomeric compounds of Formula III) as shown in Table 1.

more carriers, diluents, and excipients that are compatible with the other additives of the compositions or formulations and not deleterious to the patient. The compounds of Formula I, Formula II, and Formula III, or pharmaceutically acceptable salts thereof, described herein can be formulated as pharmaceutical compositions administered by a variety of routes, such as oral or IV. Bioavailability is often a factor in cancer treatment and the ability to choose administration methods and pharmaceutical compositions to control or optimize the bioavailability of an active ingredient is useful. For example, an orally bioavailable SERD composition would be particularly useful. The compounds of Formula I, Formula II, and Formula III, or pharmaceutically acceptable salts thereof, as described herein are believed to have bioavailability. Examples of pharmaceutical compositions and processes for their preparation can be found in "Remington: The Science and Practice of Pharmacy", L. V. Allen Jr, Editor, 22nd Ed., Mack Publishing Co., 2012. Non-limiting examples of pharmaceutically acceptable carriers, diluents, and excipients include the following: saline, water, starch, sugars, mannitol, and silica derivatives; binding agents such as carboxymethyl cellulose and other cellulose derivatives, alginates, gelatin, and polyvinyl-pyrrolidone; kaolin and bentonite; and polyethyl glycols.

Further described herein are methods of treating a cancer. The methods described herein include administering to a patient in need of such treatment an effective amount of a compound of Formula I, Formula II, and Formula III as described herein, or a pharmaceutically acceptable salt

TABLE 1

Enantiomeric forms of compounds of Formula I

| Chemical Name | R-enantiomer (Formula II) | S-enantiomer (Formula III) |
|---|---|---|
| [5-[4-[2-[3-(fluoromethyl) azetidin-1-yl]ethoxy]phenyl]-8-(trifluoromethyl)-5H-chromeno[4,3-c]quinolin-2-yl] hydrogen sulfate | (structure) | (structure) |
| (2S,3S,4S,5R,6S)-6-[[5-[4-[2-[3-(fluoromethyl) azetidin-1-yl]ethoxy]phenyl]-8-(trifluoromethyl)-5H-chromeno[4,3-c]quinolin-2-yl]oxy]-3,4,5-trihydroxy-tetrahydropyran-2-carboxylic acid | (structure) | (structure) |

Also described herein are pharmaceutical compositions comprising the compounds of Formula I, Formula II, and Formula III as described herein, or pharmaceutically acceptable salts thereof, with one or more pharmaceutically acceptable carriers, diluents, or excipients. The pharmaceutical compositions described herein may be prepared using pharmaceutically acceptable additives. The term "pharmaceutically acceptable additive(s)" as used herein, refers to one or thereof, or a pharmaceutical composition thereof. For example, the method of administering the effective amount of a compound of Formula I, Formula II, and Formula III as described herein, or a pharmaceutically acceptable salt thereof, or pharmaceutical compositions thereof, can be oral administration or alternatively, can be intravenous administration. The cancer can be breast cancer, ovarian cancer, endometrial cancer, prostate cancer, uterine cancer, gastric cancer, or lung cancer. In particular, the cancer can be an estrogen responsive cancer, for example, ER-positive breast cancer, ER-positive gastric cancer, or ER-positive lung cancer.

Also described herein are compounds of Formula I, Formula II, and Formula III as described herein, or pharmaceutically acceptable salts thereof, or a pharmaceutical composition thereof, for use in therapy. Also provided herein are the compounds of Formula I, Formula II, and Formula III as described herein, or pharmaceutically acceptable salts thereof, or a pharmaceutical composition thereof, for use in the treatment of breast cancer, ovarian cancer, endometrial cancer, prostate cancer, uterine cancer, gastric cancer, or lung cancer. In particular, the cancer can be ER-positive breast cancer, ER-positive gastric cancer, or ER-positive lung cancer. For example, the compound of Formula I, Formula II, and Formula III, or pharmaceutically acceptable salt thereof, or a pharmaceutical composition thereof, can be orally administered.

Additionally, the compounds of Formula I, Formula II, and Formula III as described herein, or pharmaceutically acceptable salts thereof, or a pharmaceutical composition thereof, can be used in the manufacture of a medicament for the treatment of a cancer. For example, the medicament can be orally administered. The types of cancer the medicaments as described herein can be used to treat include breast cancer, ovarian cancer, endometrial cancer, prostate cancer, uterine cancer, gastric cancer, or lung cancer. In particular, the cancer can be ER-positive breast cancer, ER-positive gastric cancer, or ER-positive lung cancer.

The compounds of Formula I, Formula II, and Formula III as described herein, and pharmaceutically acceptable salts thereof, or a pharmaceutical composition thereof, may have clinical utility as a single agent or in combination with one or more other therapeutic agents (e.g., anti-cancer agents), for the treatment of cancers such as breast cancer, ovarian cancer, endometrial cancer, prostate cancer, uterine cancer, gastric cancer, or lung cancer. When used in combination with other therapeutic agents (such as anti-cancer agents), the compounds of Formula I, Formula II, and Formula III as described herein, or pharmaceutically acceptable salts thereof, or a pharmaceutical composition thereof, can be used simultaneously, sequentially, or separately with other therapeutic agents. Examples of classes of drugs that the compounds of Formula I, Formula II, and Formula III as described herein, or pharmaceutically acceptable salts thereof, can be combined with include SERMs, aromatase inhibitors, CDK4 inhibitors, CDK6 inhibitors, PI3K inhibitors, and mTOR inhibitors to treat hormone receptor-positive breast cancer. More specific examples of drugs with which the compounds of Formula I, Formula II, and Formula III as described herein, or pharmaceutically acceptable salts thereof, or a pharmaceutical composition thereof, can be combined include abemaciclib (CDK4/6 inhibitor), everolimus (mTOR inhibitor), alpelisib (PIK3 CA inhibitor), and 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one (PI3K/mTOR inhibitor).

As used herein, the term "effective amount" refers to the amount or dose of a compound of Formula I, Formula II, and Formula III as described herein, or a pharmaceutically acceptable salt thereof, or a pharmaceutical composition thereof, which, upon single or multiple dose administration to the patient, provides the desired effect in the patient under diagnosis or treatment. Preferably, a desired effect is inhibition of tumor cell proliferation, tumor cell death, or both. The compounds of Formula I, Formula II, and Formula III as described herein, or pharmaceutically acceptable salts thereof, or a pharmaceutical composition thereof, are generally effective over a wide dosage range. For example, dosages per day normally fall within the daily range of about 100 mg to about 2000 mg.

As used herein, "treat", "treating" or "treatment" refers to restraining, slowing, stopping, or reversing the progression or severity of an existing symptom or disorder.

As used herein, the term "patient" refers to a human which is afflicted with a particular disease, disorder, or condition.

The compounds of Formula I, Formula II, and Formula III as described herein, or pharmaceutically acceptable salts thereof, may be prepared by a variety of procedures known in the art, some of which are illustrated in the Preparations and Examples below. The specific synthetic steps for each of the routes described may be combined in different ways, or in conjunction with steps from different procedures, to prepare compounds of Formula I, Formula II, and Formula III as described herein, or pharmaceutically acceptable salts thereof. The products can be recovered by conventional methods well known in the art, including extraction, evaporation, precipitation, chromatography, filtration, trituration, and crystallization. The reagents and starting materials are readily available to one of ordinary skill in the art.

Intermediates and processes useful for the synthesis of the compounds of Formula I, Formula II, and Formula III as described herein are intended to be included in this description. Additionally, certain intermediates described herein may contain one or more protecting groups. The variable protecting group may be the same or different in each occurrence depending on the particular reaction conditions and the particular transformations to be performed. The protection and deprotection conditions are well known to the skilled artisan and are described in the literature (See for example "Greene's Protective Groups in Organic Synthesis", Fourth Edition, by Peter G. M. Wuts and Theodora W. Greene, John Wiley and Sons, Inc. 2007).

Individual isomers, enantiomers, and diastereomers may be separated or resolved by one of ordinary skill in the art at any convenient point in the synthesis of compounds of Formula I, Formula II, and Formula III as described herein, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). While individual isomers, enantiomers, and diastereomers may be separated or resolved as noted, their Cahn-Ingold-Prelog (R) or (S) designations for chiral centers may not yet have been determined. Where Cahn-Ingold-Prelog (R) or (S) designations are not available, the identifiers "isomer 1" and "isomer 2" are used and are combined with the IUPAC name without Cahn-Ingold-Prelog stereochemistry designation. The compounds of Formula I, Formula II, and Formula III being identified as "isomer 1" or "isomer 2" herein are isolated as defined in the specific experimental descriptions below. Whether an isomer is a "1" or a "2" refers to the order in which the compounds of Formula I, Formula II, and Formula III elute from a chiral chromatography column, under the conditions listed, i.e., an "isomer 1" is the first to elute from the column under the noted conditions. If chiral chromatography is initiated early in the synthesis, the same designation is applied to subsequent intermediates and compounds of Formula I, Formula II, and Formula III.

Unless specifically noted, abbreviations used herein are defined according to *Aldrichimica Acta*, Vol. 17, No. 1, 1984. Other abbreviations are defined as follows: "BSA" refers to Bovine Serum Albumin; "CRISPR" refers to clustered regularly interspaced short palindromic repeats; "DCM" refers to dichloromethane or methylene chloride; "DMEA" refers to dimethylethanolamine; "DMEM" refers to Dulbecco's Modified Eagle's Medium; "DMF" refers to N,N-dimethylformamide; "DMSO" refers to dimethyl sulfoxide; "DNA" refers to deoxyribonucleic acid; "ee" refers to enantiomeric excess; "ER" refers to estrogen receptor; "ERα" refers to estrogen receptor alpha; "ES/MS" refers to electrospray ionization/mass spectrometry; "EtOAc" refers to ethyl acetate; "EtOH" refers to ethanol or ethyl alcohol; "FBS" refers to Fetal Bovine Serum; "HCl" refers to hydrochloric acid; "$IC_{50}$" refers to the concentration of an agent which produces 50% of the maximal inhibitory response possible for that agent, (relative $IC_{50}$), or the concentration of an agent which produces 50% inhibition of the target enzyme activity compared to placebo control (absolute $IC_{50}$); "iPrOH" refers to isopropanol or isopropyl alcohol; "IV" refers to intravenous administration; "LC/MS" refers to liquid chromatography/mass spectrometry; "MeOH" refers to methyl alcohol or methanol; "MTBE" refers to methyl t-butyl ether; "m/z" refers to mass to charge ratio; "PBS" refers to Phosphate Buffered Saline; "PR" refers to progesterone receptor; "PRa" refers to progesterone receptor alpha; "RNase" refers to ribonuclease; "SIT" refers to supercritical fluid chromatography; "THF" refers to tetrahydrofuran; "$t_{(R)}$" refers to retention time; and "XPhos Pd G2" refers to chloro(2-dicyclohexylphosphino-2',4',6'-triisopropyl-1,1'-biphenyl)[2-(2'-amino-1,1'-biphenyl)]palladium (II).

The following preparations and examples further illustrate the invention.

PREPARATIONS AND EXAMPLES

Scheme 1 depicts the synthesis of compounds of Formula I, II or III.

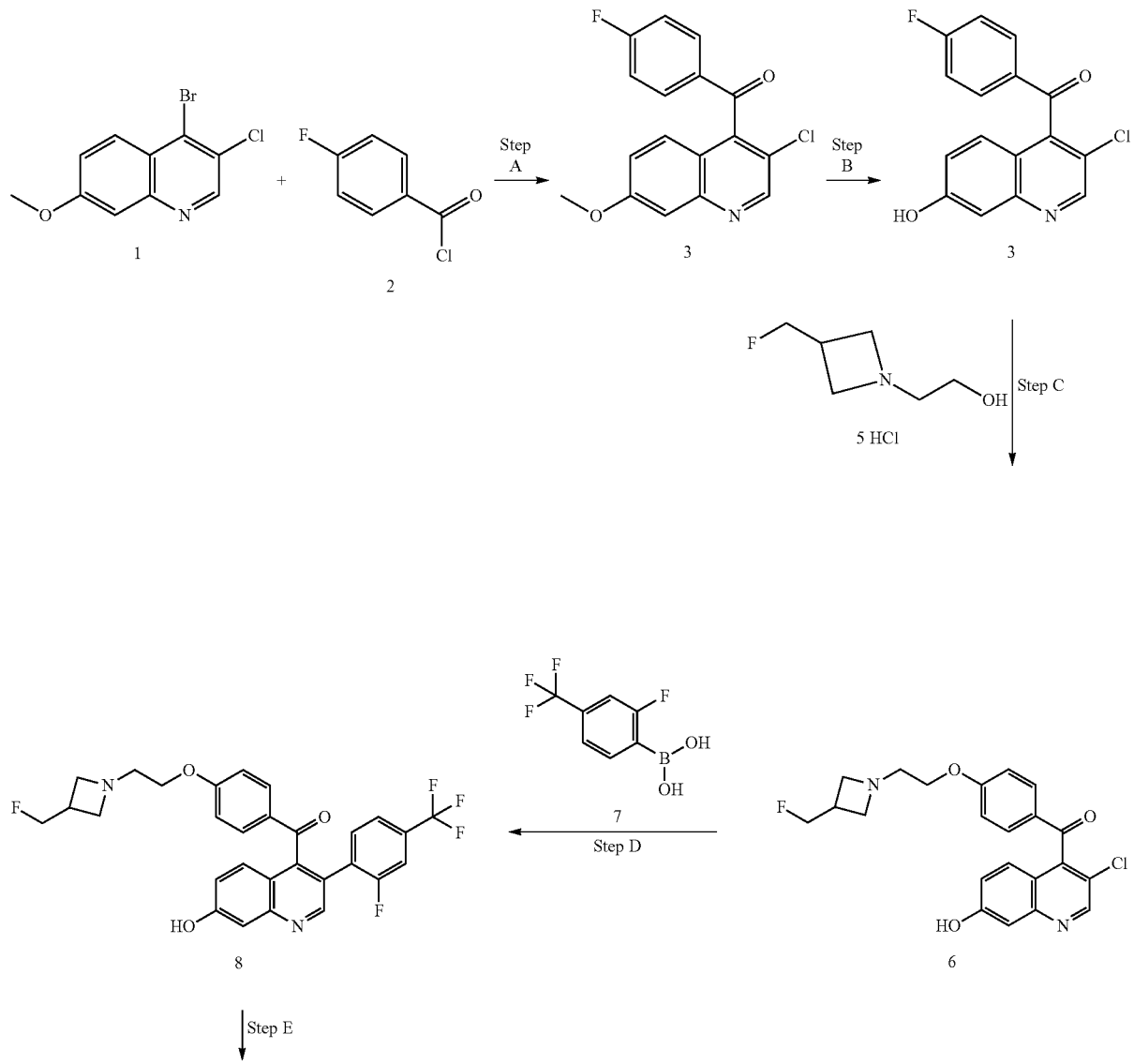

-continued

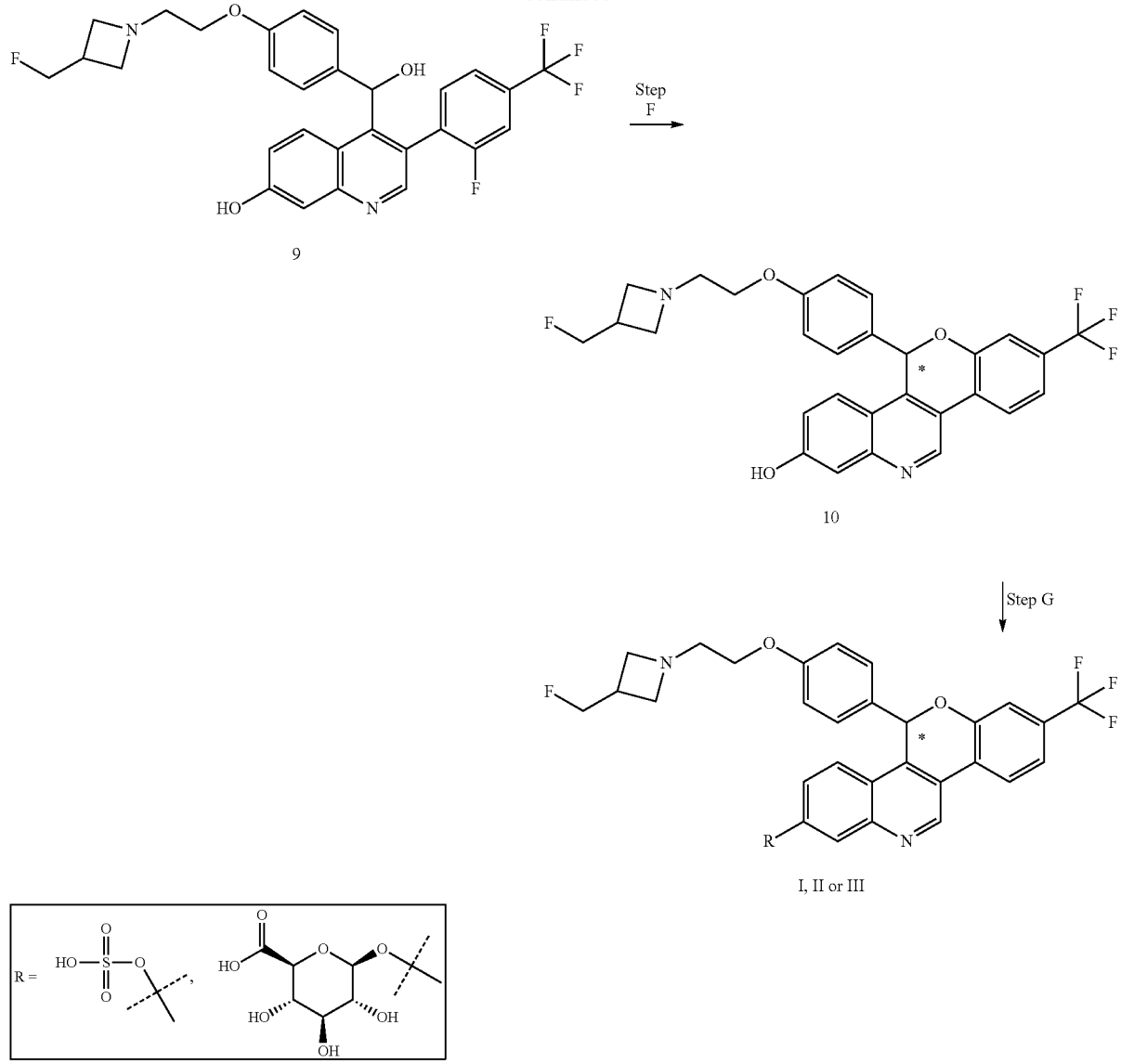

In Step A, a Grignard reaction is accomplished. A Grignard reaction is well known in the art as a reaction for the formation of carbon-carbon bonds. The reaction involves an organometallic reaction in which an aryl magnesium halide, the Grignard reagent adds to a carbonyl group such as the acid chloride of compound 2 to give the compound of Step A. For example, a 4-chloro-substituted quinolone, compound 1, is treated with a Grignard reagent such as isopropylmagnesium chloride to form a Grignard intermediate followed by the addition of an acid chloride, 4-fluorobenzoyl chloride, compound 2, in a solvent such as THF. At completion, the reaction can be quenched with water to give compound 3.

In Step B, the aryl methyl ether of compound 3 may be demethylated under a variety of conditions recognizable to the skilled artisan such as treatment with boron tribromide. For example, compound 3 is slowly treated with boron tribromide at a temperature of about 0° C. in a solvent such as DCM. The mixture is stirred at room temperature and quenched with dibasic potassium phosphate to give compound 4.

In Step C, the azetidine ether 6 may be formed by treatment of the corresponding p-fluorophenyl ketone 4 and the azetidine alcohol salt 5, or the corresponding free base with a suitable base, for example sodium hydride, sodium t-butoxide or potassium t-butoxide, in the appropriate polar aprotic solvent such as DMF or THF to give the ether compound 6.

Compound 6 is then alkylated with the appropriate substituted aryl boronic acid, compound 7, in a Suzuki cross coupling reaction to give compound 8 in Step D. The skilled artisan will recognize that there are a variety of conditions that may be useful for facilitating such cross-coupling reactions. Suitable palladium reagents may include XantPhos Pd G2, cataCXium® A Pd G3, bis(triphenylphosphine)palladium(II) chloride, tris(dibenzylideneacetone)dipalladium (0) with tricyclohexylphosphine, (1,1'-bis(diphenylphosphino)ferrocene)palladium(II) chloride, palladium tetrakistriphenylphosphine, or palladium(II) acetate. Suitable bases may include potassium fluoride, cesium carbonate, sodium carbonate, potassium carbonate, lithium t-butoxide, or potassium phosphate tribasic monohydrate. Compound 6, for example, can be reacted with the appropriate boronic acid, compound 7, such as 2-fluoro-4-(trifluoromethyl)phenylboronic acid in a solvent such as 2-methyl-2-butanol with a base such as potassium carbonate and a catalyst such as XPhos Pd G2 and heated to about 80° C. under microwave conditions to give compound 8.

One skilled in the art will recognize that Step D, the Suzuki cross coupling reaction, could be completed before the azetidine ether formation of Step C.

In Step E, one skilled in the art will recognize that compound 9 may be obtained by reduction of the ketone. This can be accomplished using a reducing agent, such as lithium triethyl borohydride in solvents such as 1,4-dioxane and THF and at a temperature of about 0° C. to room temperature to give the corresponding secondary alcohol 9 which can optionally be purified by chiral chromatography to give an enantiomerically enriched secondary alcohol.

In Step F, alcohol 9 may be subjected to an intramolecular cyclization by reaction with a base, such as sodium hydride, to yield cyclic ether 10. The skilled person will recognize that a variety of suitable bases can be employed for this step.

In Step G, further reaction of alcohol 10 with either sulfur trioxide trimethylamine complex or acetobromo-α-D-glucuronic acid methyl ester followed by ester hydrolysis gives the compounds of Formula I, II or III In an optional step, a pharmaceutically acceptable salt of a compound of Formula I, Formula II, and Formula III as described herein can be formed by reaction of an appropriate free base of a compound of Formula I, Formula II, and Formula III as described herein with an appropriate pharmaceutically acceptable acid in a suitable solvent under standard conditions. Additionally, the formation of such salts can occur simultaneously upon deprotection of a nitrogen-protecting group. The possible formation of pharmaceutically acceptable salts is well known. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977). One of ordinary skill in the art will appreciate that a compound of Formula I, Formula II, and Formula III as described herein is readily converted to and may be isolated as a pharmaceutically acceptable salt. Examples of useful salts include, but are not limited to, benzenesulfonic acid salts and 4-methylbenzenesulfonic acid salts. 4-methylbenzenesulfonic acid salts are also known as tosylate salts.

Preparation 1

2-[3-(Fluoromethyl)azetidin-1-yl]ethan-1-ol

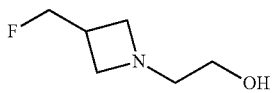

Add sodium triacetoxyborohydride (405 g, 1.91 mol) portion-wise over a period of 15 minutes to a stirred 0° C. solution of 3-(fluoromethyl)azetidine hydrochloride (160 g, 1.28 mol) in DCM (2.4 L) under nitrogen gas and stir at 0° C. for 10 minutes. Add 1,4-dioxane-2,5-diol (99 g, 0.83 mol) at 0° C. in 6 portions over a period of 1 hour then stir at 0-5° C. for 15 minutes. Allow the reaction to warm to room temperature and stir for 2 hours under nitrogen gas. Cool the reaction to 10-15° C. over a period of 20 minutes, then warm to 25-30° C. and maintain at this temperature for 2 hours. Add water (800 mL) over a period of 25-30 minutes at 10-15° C., allow to warm to room temperature for 5-10 minutes and then separate the layers. Wash the aqueous layer with DCM (800 mL), separate the layers then cool the combined aqueous layers to 10-15° C. and adjust the pH to 13-14 using 50% aqueous sodium hydroxide solution (~540 mL). Allow the aqueous layer to warm to room temperature, extract with DCM (4×800 mL), dry with anhydrous Na₂SO₄, filter, and concentrate to dryness to obtain the title compound (139 g, 82%) as a thick yellow oil. ES/MS (m/z): 134.1 (M+H).

Preparation 2

2-[3-(Fluoromethyl)azetidin-1-yl]ethan-1-ol hydrochloride

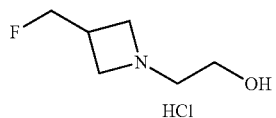

Dissolve 2-[3-(fluoromethyl)azetidin-1-yl]ethan-1-ol (529 g, 4 mol) in MTBE (2.6 L) and cool to 0° C. Add HCl/EtOH solution (492 mL, 30 wt %) dropwise over 30 minutes then stir at 0° C. for 30 minutes. Filter the solids and wash the filter cake with MTBE (2×200 mL). Dry under nitrogen gas for 8 hours to obtain the title compound (580 g, 86%) as a white solid. ES/MS (m/z): 134.0 (M+H).

Preparation 3

(3-Chloro-7-methoxyquinolin-4-yl)-(4-fluorophenyl)methanone

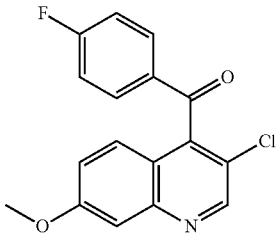 [SMILES: COc1ccc2c(C(=O)c3ccc(F)cc3)c(Cl)cnc2c1]

Cool a mixture of 4-bromo-3-chloro-7-methoxyquinoline (70 g, 254 mmol) and THF (1 L) to −40° C. under nitrogen gas resulting in precipitation of the material. Add isopropylmagnesium chloride (2 M in THF, 254 mL, 509 mmol) over 20 minutes and stir the mixture for 1 hour. Add a solution of 4-fluorobenzoyl chloride (66 mL, 559 mmol) in THF (140 mL) dropwise then allow to warm to room temperature. Quench the reaction with saturated aqueous NH₄Cl solution (300 mL) and water (200 mL) and separate the layers. Wash the organic layer with saturated aqueous NH₄Cl solution (300 mL), dry over anhydrous MgSO₄, filter, and concentrate to provide an oily residue. Filter the crude brown oil through silica gel eluting with a mixture of MTBE/hexanes (1:1) to obtain the crude product as a yellow solid (84 g). Treat the solid with 10% methylacetate/heptane (800 mL) and stir at room temperature overnight. Filter to collect the solids and reserve. Concentrate the filtrate and purify on silica gel eluting with 10-40% EtOAc/hexanes then treat the product with 10% methylacetate/heptane (200 mL) and stir at room temperature for 3 hours. Filter the resulting solids, combine with solids from the previous filtration and dry under vacuum overnight to obtain the title compound (31 g, 38%) as a yellow solid. ES/MS (m/z): 316.0 (M+H).

Preparation 4

(3-Chloro-7-hydroxyquinolin-4-yl)-(4-fluorophenyl)methanone

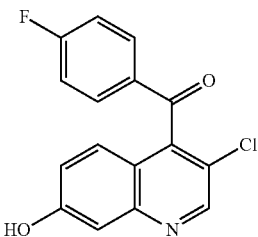 [SMILES: O=C(c1ccc(F)cc1)c1c(Cl)cnc2cc(O)ccc12]

Add boron tribromide (1 M in DCM, 295 mL, 295 mmol) to a mixture of (3-chloro-7-methoxyquinolin-4-yl)-(4-fluorophenyl)methanone (31 g, 98 mmol) in DCM (217 ml) and stir the mixture at room temperature for 3 days. Pour the mixture slowly into a 0° C. solution of aqueous dibasic potassium phosphate (2 M, 700 mL) and water (200 mL). Allow the mixture to warm to room temperature and stir for 1 hour. Concentrate the solution in vacuo to remove organic solvents, filter, collect the filtrate and dry the filtrate under vacuum at 45° C. overnight. Treat the solids with DCM/heptane (1:1, 450 mL) and stir overnight. Collect the solids and dry under vacuum overnight to obtain the title compound (32 g, quantitative yield) as a light brown solid. ES/MS (m/z): 302.0 (M+H).

Preparation 5

(3-Chloro-7-hydroxyquinolin-4-yl)-(4-{2-[3-(fluoromethyl)azetidin-1-yl]ethoxy}phenyl)methanone

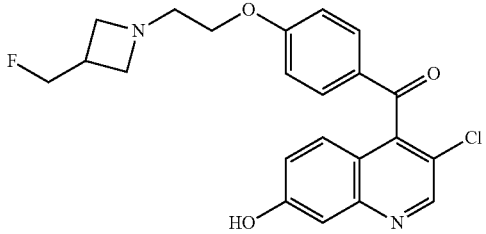 [SMILES: O=C(c1ccc(OCCN2CC(CF)C2)cc1)c1c(Cl)cnc2cc(O)ccc12]

Add 2-[3-(fluoromethyl)azetidin-1-yl]ethan-1-ol hydrochloride (3.90 g, 23.0 mmol) to a stirred solution of (3-chloro-7-hydroxyquinolin-4-yl)-(4-fluorophenyl)methanone (5.00 g, 15.3 mmol) in DMF (75 ml) followed by sodium hydride (60% in mineral oil, 3.02 g, 76.8 mmol). Stir under nitrogen gas and warm to 40° C. for 45 minutes. Quench the solution with water and concentrate. Partition the residue between 20% iPrOH/CHCl$_3$ and saturated aqueous sodium bicarbonate solution and separate, extract the aqueous with 2×20% iPrOH/CHCl$_3$, combine the organic extracts, dry the combined organic layers over magnesium sulfate, filter and concentrate the filtrate to obtain the crude product as a dark red oil. Purify the crude material by silica gel column chromatography eluting with a gradient of 5-10% 7N NH$_3$ in MeOH/DCM to give the title compound (5.31 g, 84%) as a yellow solid. ES/MS (m/z): 415.0 (M+H).

Preparation 6

(4-{2-[3-(Fluoromethyl)azetidin-1-yl]ethoxy}phenyl) {3-[2-fluoro-4-(trifluoromethyl)phenyl]-7-hydroxyquinolin-4-yl}methanone

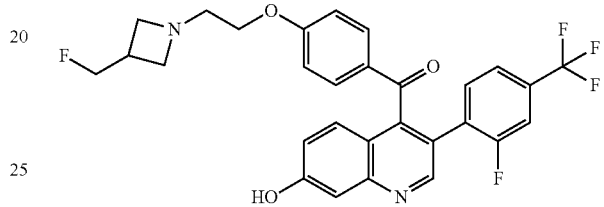

Degas with nitrogen gas (5×) a mixture (3-chloro-7-hydroxyquinolin-4-yl)-(4-{2-[3-(fluoromethyl)azetidin-1-yl]ethoxy}phenyl)methanone (200 mg, 0.48 mmol), 2-fluoro-4-(trifluoromethyl)phenylboronic acid (158 mg, 0.72 mmol), potassium carbonate (202 mg, 1.45 mmol), 2-methyl-2-butanol (3 ml), and water (1 ml) in a microwave vial. Add XPhos Pd G2 (12 mg, 0.015 mmol), seal and microwave at 80° C. for 2 hours. Partition the residue between MTBE and saturated aqueous NH$_4$Cl solution. Separate the layers and extract the aqueous with MTBE. Combine the organic extracts, dry over anhydrous MgSO$_4$, filter, and concentrate the filtrate to obtain an orange residue. Purify the crude material by silica gel column chromatography eluting with 5% MeOH/DCM to give the title compound (205 mg, 78%) as a yellow solid. ES/MS (m/z): 543.2 (M+H).

Preparation 7

Racemic 4-{2-[3-(Fluoromethyl)azetidin-1-yl]ethoxy}phenyl)(hydroxy)methyl]-3-[2-fluoro-4-(trifluoromethyl)phenyl]quinolin-7-ol

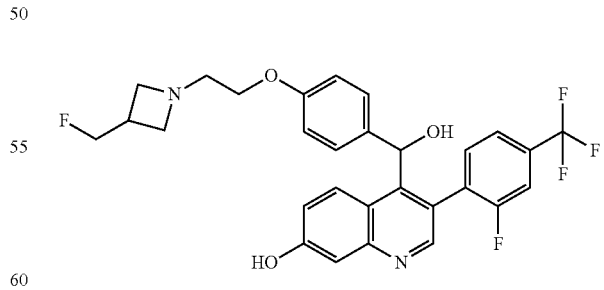

Add (4-{2-[3-(fluoromethyl)azetidin-1-yl]ethoxy}phenyl){3-[2-fluoro-4-(trifluoromethyl)phenyl]-7-hydroxyquinolin-4-yl}methanone (305 g, 562.2 mmol) and THF (1.5 L) together under nitrogen gas and cool the solution to 0-5° C. Add lithium triethylborohydride (1 M in THF, 1.5 L, 1.5 mol) dropwise. Stir the mixture at 0-5° C. for 1 hour. Add water (300 mL) dropwise and saturated aqueous NH$_4$Cl (1

L). Warm the mixture to room temperature. Add EtOAc (2 L) and collect the organic layer. Wash the organic layer with brine (500 mL), dry over anhydrous MgSO$_4$, filter, and concentrate to dryness. Dissolve the residue in 95:5 mixture of acetone and 2 M ammonia in MeOH and filter through silica gel to give the title compound (264 g, 86.2%) as an orange solid. ES/MS (m/z): 545.2 (M+H).

Preparation 8

4-[(R)-[4-[2-[3-(Fluoromethyl)azetidin-1-yl]ethoxy]phenyl]-hydroxy-methyl]-3-[2-fluoro-4-(trifluoromethyl)phenyl]quinolin-7-ol

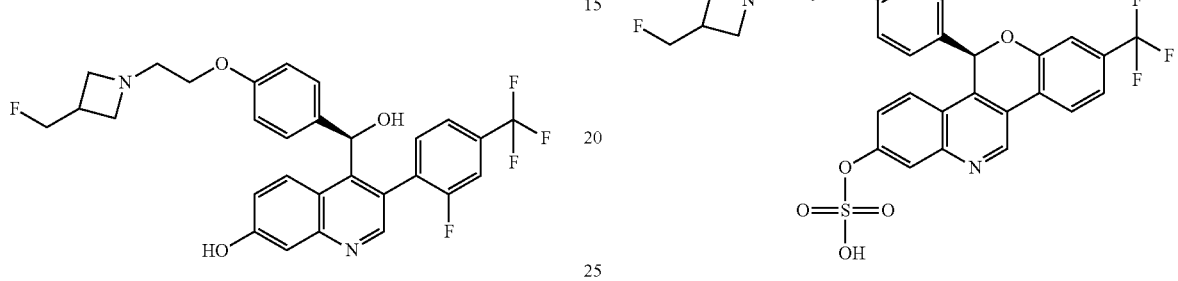

Purify Racemic 4-{2-[3-(fluoromethyl)azetidin-1-yl]ethoxy}phenyl)(hydroxy)methyl]-3-[2-fluoro-4-(trifluoromethyl)phenyl]quinolin-7-ol (5.5 g, 0.10 mol) using chiral chromatography under the following conditions: Column Chiralpak® AD-H, 150×50 mm, flow rate 200 g/minute, UV 270 nm, mobile phase 35% iPrOH with 0.5% DMEA/CO$_2$, column temperature 35° C. to give the title compound (2.6 g g, 47%). Confirm enantiomeric enrichment of Isomer 1 by chiral analytical SFC, >96% ee, $t_{(R)}$=0.79 minutes, column: 4.6×150 mm Chiralpak® AD-H, eluting with a mobile phase of 35% iPrOH with 0.5% DMEA in CO$_2$, flow rate of 0.6 mL/minute, UV detection of 350 nm.

Preparation 9

(5R)-5-[4-[2-[3-(Fluoromethyl)azetidin-1-yl]ethoxy]phenyl]-8-(trifluoromethyl)-5H-chromeno[4,3-c]quinolin-2-ol

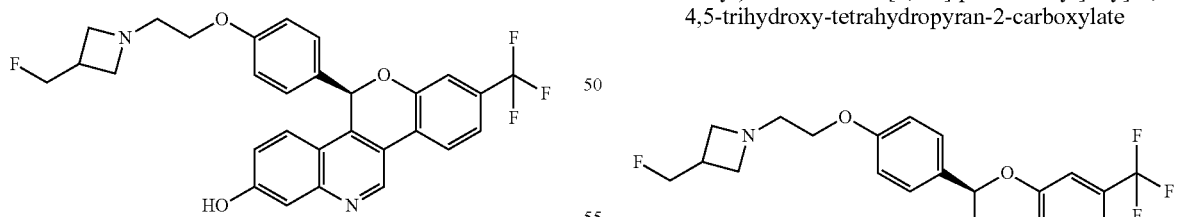

Add sodium hydride (60% dispersion in mineral oil, 1.00 g, 15 mmol) to a stirred solution of 4-[(R)-[4-[2-[3-(fluoromethyl)azetidin-1-yl]ethoxy]phenyl]-hydroxy-methyl]-3-[2-fluoro-4-(trifluoromethyl)phenyl]quinolin-7-ol (2.60 g, 5 mmol) in THF (50 mL) and warm the resulting solution to 65° C. under nitrogen gas. After 1 hour the reaction is cooled to room temperature and then quenched with water (50 mL). The resulting mixture is partitioned between EtOAc (50 mL1) and saturated aqueous NH$_4$Cl (50 mL). The layers are separated and the aqueous phase is extracted with fresh EtOAc (50 mL). The combined organic layers are dried over anhydrous MgSO$_4$, filtered and concentrated to give a yellow solid. The crude mixture is purified by column chromatography (4-6% MeOH/DCM) to obtain the title compound as a yellow solid (1.98 g, 80%). ES/MS (m/z): 525.2 (M+H).

EXAMPLE 1

[(5R)-5-[4-[2-[3-(Fluoromethyl)azetidin-1-yl]ethoxy]phenyl]-8-(trifluoromethyl)-5H-chromeno[4,3-c]quinolin-2-yl]hydrogen sulfate

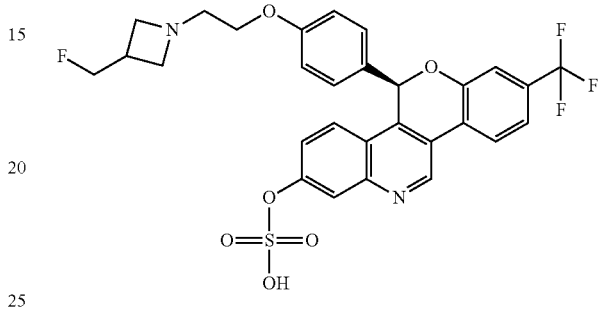

Sodium methoxide solution in MeOH (0.5 M, 0.6 mL, 0.3 mmol) is added to a solution of (5R)-5-[4-[2-[3-(fluoromethyl)azetidin-1-yl]ethoxy]phenyl]-8-(trifluoromethyl)-5H-chromeno[4,3-c]quinolin-2-ol (54 mg, 0.1 mmol) in anhydrous THF (10 mL). After stirring at room temperature for 0.5 hours, sulfur trioxide trimethylamine complex (57 mg, 0.4 mmol) is added every hour in four equal portions over 4 h. The solvent is then evaporated under a stream of nitrogen gas and the reaction mixture is diluted with water (5 mL). Aqueous NaOH (1 M, 2 drops) is added adjusting the pH to 8. The solution is directly loaded onto an Iterchim automated chromatography system (30 g RediSep® Rf Gold reverse-phase C18 column), eluting with a gradient of 10 to 90% acetonitrile in water to give the title product (46 mg, 74%) as a light-yellow solid. ES/MS (m/z): 605.6 (M+H).

Preparation 10

Methyl (2S,3S,4S,5R,6S)-6-[[(5R)-5-[4-[2-[3-(fluoromethyl)azetidin-1-yl]ethoxy]phenyl]-8-(trifluoromethyl)-5H-chromeno[4,3-c]quinolin-2-yl]oxy]-3,4,5-trihydroxy-tetrahydropyran-2-carboxylate

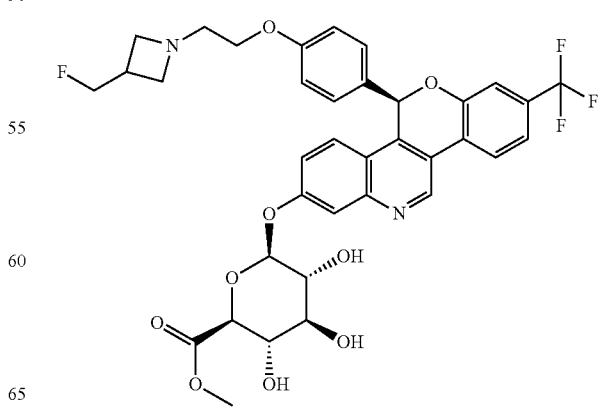

Lithium hydroxide (90.9 mg, 3.80 mmol) is added to a suspension of (5R)-5-[4-[2-[3-(fluoromethyl)azetidin-1-yl]ethoxy]phenyl]-8-(trifluoromethyl)-5H-chromeno[4,3-c]quinolin-2-ol (830.0 mg, 1.58 mmol) in anhydrous MeOH (16 mL) at room temperature. The mixture is stirred until the starting material dissolved (around 20 min). Acetobromo-α-D-glucuronic acid methyl ester (1.19 g, 3.01 mmol) is added. The reaction is stirred at room temperature for 4 hours at which point LC/MS analysis of the reaction mixture indicates 28% conversion to the desired product and 60% unreacted starting material. Additional lithium hydroxide (92.0 mg, 3.84 mmol) is added. After stirring for 10 minutes, additional acetobromo-α-D-glucuronic acid methyl ester (1.19 g, 3.01 mmol) is added. After an additional 3 hours, LC/MS analysis indicates 35% conversion to product and 50% unreacted starting material. The reaction is discontinued and the mixture is used in the subsequent step without purification.

EXAMPLE 2

(2S,3S,4S,5R,6S)-6-[[(5R)-5-[4-[2-[3-(Fluoromethyl)azetidin-1-yl]ethoxy]phenyl]-8-(trifluoromethyl)-5H-chromeno[4,3-c]quinolin-2-yl]oxy]-3,4,5-trihydroxy-tetrahydropyran-2-carboxylic acid

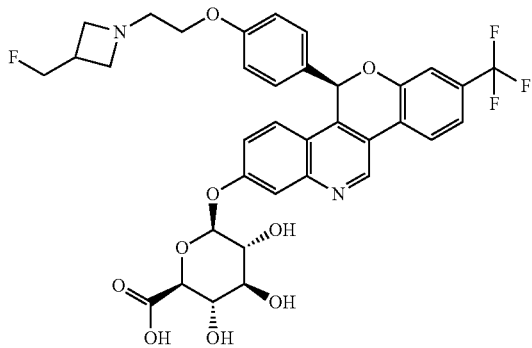 [SMILES: O=C(O)[C@H]1O[C@@H](Oc2ccc3c4c(cnc3c2)-c2ccc(C(F)(F)F)cc2O[C@@H]4c2ccc(OCCN3CC(CF)C3)cc2)[C@H](O)[C@@H](O)[C@@H]1O]

The reaction mixture from Preparation 10 is added to a solution of lithium hydroxide (114.5 mg, 4.78 mmol) in water (10 mL). The reaction is stirred for 2 hours at which point LC/MS analysis of the reaction mixture indicates the hydrolysis is not complete. Additional lithium hydroxide (114.5 mg, 4.78 mmol) and MeOH (8 mL) are sequentially added. The reaction is stirred at room temperature for 1.5 hours and LC/MS analysis indicates the hydrolysis reaction is complete. The pH of the mixture is adjusted to pH 7 with concentrated acetic acid and separated into two equal portions. Each portion is loaded onto a reverse phase C18 column (275 g RediSep® Rf Gold reverse-phase C18 column) eluting with a gradient of 0 to 100% acetonitrile in water. The fractions are combined and concentrated under reduced pressure at 25° C. The residue is lyophilized to give the title compound as a light-yellow solid (80 mg, 7% yield over two steps). ES/MS (m/z): 701.6 (M+H).

Biological Assays

The evidence for a relationship between ER expression and certain cancers is well known in the art.

The results of the following assays demonstrate that the compounds of Formula I, Formula II, and Formula III of the examples are active SERDs and are conceived to be useful in treating cancer.

ERα Degradation Assay in MCF7 Cells

The purpose of the following ERα degradation assay is to measure the degradation of ERα by a test compound in an ERα positive breast cancer cell line such as MCF7.

Culture MCF7 (purchased from ATCC HTB-22) cells in DMEM media supplemented with 10% FBS, 0.01 mg/mL human insulin 1 and 1% penicillin/streptomycin antibiotics and plate in 384-well flat-bottom plates at a density of 4,000 cells per well in phenol red free DMEM media (20 μL) containing 10% charcoal stripped FBS. Incubate the cells overnight in a cell culture incubator (5% $CO_2$, 95% relative humidity and 37° C.) and allow the cells to attach to the plate. The following day dose the cells with the test compound. Use an Echo 555 acoustic dispenser to prepare test compound serial dilutions (1:3) in a range from 6 μM to 0.0003 μM. Dose the cells with the addition of 5 μL from the serial dilution plate to the cell plate producing a final DMSO concentration of 0.2% with a final test compound concentration dose range between 2 and 0.0001 μM. For the maximum point, use media containing 0.2% of DMSO and for the minimum point, use fulvestrant diluted at 2 μM final concentrations in the growth media containing 0.2% DMSO. After dosing with the test compound, incubate the cell plates at 37° C. and 5% $CO_2$ for 24 hours. Fix the cells by adding 14% paraformaldehyde (10 μL) for 30 minutes at room temperature. Wash the cells once with PBS (20 μL) and incubate with PBS (20 μL) containing 0.5% (v/v) TWEEN® 20 for 1 hour. Wash the cells with PBS containing 0.05% TWEEN® 20 (2×) and block with 3% BSA in PBS containing 0.05% TWEEN® 20 and 0.1% TRITON™ X-100 (20 μL/well) for 1 hour at room temperature. Add 1:500 Primary antibody (20 μL) (ERα (Clone SP1) monoclonal rabbit antibody #RM-9101-S, Thermo Scientific) dilution in 1% BSA in PBS containing 0.05% TWEEN® 20 per well, seal the plates and incubate overnight at 4° C. The following day wash the cells with PBS containing 0.05% TWEEN® 20 (2×) and incubate with secondary antibody (20 μL/well) (1:1000 dilution, Goat anti-rabbit IgM ALEXA FLUOR™ 488) in PBS 1% BSA for 105 minutes at room temperature. After washing plates with PBS (2×20 μL), add RNase (Sigma) (20 μL of 50 μg/mL) and 1:1000 propidium iodide dilution in PBS per well (20 μL). Seal the plates and incubate 1 hour at room temperature on the bench (preserved from light). Scan the plates with ACUMEN EXPLORER™ (Laser-scanning fluorescence microplate cytometer manufactured by TTP LABTECH LTD) to measure ERα. Image analysis is based on cellular fluorescent signals for identifying positive cells. Identify ER positive cells by mean intensity. Use total intensity at 575-640 nm from propidium iodide/DNA to identify individual cells. Assay output is % ER positive cells. Determine the $IC_{50}$ by curve fitting to a four parameter logistic for each output using GENE DATA™. The relative $IC_{50}$ values for Examples 1 and 2 are shown in Table 2. The results of this assay demonstrate degradation of ERα induced by Examples 1 and 2 as described herein in MCF7 breast cancer cells.

TABLE 2

ERα degradation assay in MCF7 cells

| Example # | Relative IC$_{50}$ (μM) |
|---|---|
| 1 | 0.115 ± 0.0184, n = 4 |
| 2 | 0.211 ± 0.0692, n = 4 |

PRα Induction Assay in MCF7 Cells

The purpose of the following PRα induction assay is to determine whether a test compound has agonistic activity against ERα receptor (an agonist would be expected to activate the receptor).

Culture MCF7 (purchased from ATCC HTB-22) in DMEM media supplemented with 10% FBS, 0.01 mg/mL human insulin 1 and 1% penicillin/streptomycin antibiotics and plate the cells (prior to becoming 70% confluent) in 384-well flat-bottom plates at a density of 4,000 cells per well in 20 μL volume in DMEM phenol red free media containing 10% FBS (charcoal stripped). Incubate the cells overnight in a cell culture incubator (5% $CO_2$, 95% relative humidity at 37° C.) and allow the cells to attach to the plate. The following day dose the cells with test compound. Use an Echo 555 acoustic dispenser to prepare compound serial dilutions (1:3) in a range from 6 μM to 0.0003 μM. Dose the cells with the addition of the test compound (5 μL) from the serial dilution plate to the cell plate producing a final DMSO concentration of 0.2% with a final concentration of the test compound dose range between 2 and 0.0001 μM. For the maximum point use media containing 0.2% of DMSO and for the minimum point, use fulvestrant diluted at 2 μM final concentrations in the growth media containing 0.2% DMSO. After dosing with the test compound, incubate the cell plates at 37° C. and 5% $CO_2$ for 24 hours. Fix the cells by adding 14% paraformaldehyde (10 μL) for 30 minutes at room temperature. Wash cells once with PBS (20 μL) and incubate with PBS (20 μL) containing 0.5% (v/v) TWEEN® 20 for 1 hour. Wash cells twice with PBS (20 μL) containing 0.05% TWEEN® 20 and block with 3% BSA in PBS containing 0.05% TWEEN® 20 and 0.1% TRITON™ X-100 (20 μL/well) for 1 hour at room temperature. Add 1:500 primary antibody (20 μL) (PR monoclonal mouse anti-human antibody, clone PgR 636 Dako, M3569) dilution in 1% BSA/PBS with 0.05 TWEEN® 20 per well, seal the plates and incubate overnight at 4° C.

The following day wash cells with PBS 0.05% TWEEN® 20 (2×20 μL) and incubate with secondary antibody (20 μL/well) (1:1000 dilution, Goat anti-rabbit IgM ALEXA FLUOR™ 488) in PBS 1% BSA for 105 minutes at room temperature. After washing with PBS (2×20 μL), add RNase (20 μL of 50 μg/mL) (Sigma) and 1:1000 propidium iodide dilution in PBS per well. Seal plates and incubate 1 hour at room temperature on the bench (preserved from light). Scan plates with ACUMEN EXPLORER™ (Laser-scanning fluorescence microplate cytometer manufactured by TTP LABTECH LTD) to measure PRα. Image analysis is based on cellular fluorescent signals for identifying positive cells. Identify PR positive cells by mean intensity. Use total intensity at 575-640 nm from propidium iodide/DNA to identify individual cells. Assay output is % PR positive cells. Determine the IC$_{50}$ by curve fitting to a four parameter logistic for each output using GENE DATA™. The results of this assay demonstrate no significant agonistic activity of Examples 1 and 2 in MCF7 breast cancer cells. For the compounds tested, the Relative IC$_{50s}$ in this assay are >2 μM. The results of this assay demonstrate no significant agonistic activity of the exemplified compounds tested in MCF7 breast cancer cells. These results also demonstrate that the exemplified compounds tested are antagonists of ERα in MCF7 breast cancer cells (i.e., they have SERD activity).

PRα Inhibition (ERα Functional Antagonism) Cell Assay in MCF7-ESR1 Y537N 682 CRISPR Cells The purpose of the following PRα inhibition (ERα functional antagonism) cell assay is to determine the antagonistic activity of a test compound against the Y537N mutant ERα receptor. An antagonist in this assay is expected to block the function of the ERα receptor. PRα is a downstream transcriptional target of ERα and hence an antagonist of ERα is expected to inhibit the expression of PRα.

Culture MCF7-ESR1 Y537N-682 (generated by CRISPR/Cas9 gene editing of ESR1 gene in MCF7 cells, clone #682) in DMEM media supplemented with 10% FBS and 1% penicillin/streptomycin antibiotics and plate the cells (prior to becoming 70% confluent) in 384-well flat-bottom plates at a density of 4,000 cells per well in DMEM phenol red free media 10% FBS (20 μL volume) (charcoal stripped). Incubate the cells overnight in a cell culture incubator (5% $CO_2$, 95% relative humidity and 37° C.) and allow the cells to attach to the plate. The following day dose the cells with the test compound. Use an Echo 555 acoustic dispenser to prepare compound serial dilutions (1:3) in a range from 6 μM to 0.0003 μM. Dose the cells with the addition of 5 μL from the serial dilution plate to the cell plate producing a final DMSO concentration of 0.2% with a final test compound concentration dose range between 2 and 0.0001 μM. For the maximum point use media containing 0.2% of DMSO and for the minimum point, use fulvestrant diluted at 2 μM final concentrations in the growth media containing 0.2% DMSO. After dosing with test compound, incubate the cell plates at 37° C. and 5% $CO_2$ for 72 hours. Fix the cells by adding 14% paraformaldehyde (10 μL) for 30 minutes at room temperature. Wash the cells with PBS (1×20 μL) and incubate with PBS (20 μL) of containing 0.5% (v/v) TWEEN® 20 for 1 hour. Wash the cells with PBS (2×20 μL), 0.05% TWEEN® 20, and block with 3% BSA/PBS 0.05% TWEEN® 20, 0.1% TRITON™ X-100 (20 μL/well) for 1 hour at room temperature. Add 1:500 primary antibody (20 μL) (PR monoclonal mouse anti-human antibody, clone PgR 636 Dako, M3569) dilution in 1% BSA/PBS 0.05 TWEEN® 20 per well, seal the plates and incubate overnight at 4° C.

The following day wash the cells with PBS 0.05%® (2×20 μL) and incubate with secondary antibody (20 μL/well) (1:1000 dilution, Goat anti-rabbit IgM ALEXA FLUOR™ 488) in PBS 1% BSA for 105 minutes at room temperature. After washing with PBS (2×20 μL), add RNase (20 μL of 50 μg/mL) (Sigma) and 1:1000 propidium iodide dilution in PBS per well. Seal plates and incubate 1 hour at room temperature on the bench (preserved from light). Scan the plates with ACUMEN EXPLORER™ [Laser-scanning fluorescence microplate cytometer manufactured by TTP LABTECH LTD] to measure PRα. Image analysis is based on cellular fluorescent signals for identifying positive cells. Identify PR positive cells by mean intensity. Use total intensity at 575-640 nm from propidium iodide/DNA to identify individual cells. Assay output is % PR positive cells. Determine the IC$_{50}$ by curve fitting to a four parameter logistic for each output using GENE DATA™.

The Relative IC$_{50}$s of Examples 1 and 2 in this assay are shown in Table 3 below. The results of this assay demonstrate inhibition of PRα and functional antagonism by Examples 1 and 2 in MCF7 (ESR1 Y537N, heterozygous mutant) breast cancer cells. PRα (PGR) is also a transcriptional target of ERα and the results from this assay demonstrate inhibition of ERα-mediated transcription of PRα.

TABLE 3

PRα inhibition (ERα functional antagonism) cell assay in MCF7 Y537N 682 CRISPR cells

| Example # | Relative IC$_{50}$ (μM) |
|---|---|
| 1 | 0.330 ± 0.116, n = 3 |
| 2 | 0.470 ± 0.058, n = 3 |

Cell Proliferation Assay in MCF7 and MCF7-ESR1 Y537N-682

The purpose of the following cell proliferation assays generally is to detect whether a test compound has effects on cell proliferation.

Seed MCF7 (purchased from ATCC HTB-22) cells at a density of 2,000 cells per well in DMEM phenol red free media 10% FBS (20 μL volume) (charcoal stripped) into a clear bottom 384-well cell culture plate. Plate MCF7-ESRY537N-682 (generated by CRISPR/Cas9 gene editing of ESr1 gene in MCF7 cells, clone #682) in DMEM media supplemented with 10% FBS, and 1% penicillin/streptomycin antibiotics at a density of 1000 cells per well. Incubate the plates at 37° C. and 5% CO$_2$. The following day dose the cells with the test compound. Use an Echo 555 acoustic dispenser to prepare test compound serial dilutions (1:3) in a range from 60 μM to 0.003 μM. Dose the cells with the addition of 5 μL from the serial dilution plate to the cell plate, producing a final DMSO concentration of 0.2% with a final test compound concentration dose range between 20 and 0.001 μM. For the maximum point use media containing 0.2% of DMSO and for the minimum point use fulvestrant diluted at 2 μM final concentrations in the growth media containing 0.2% DMSO. After dosing with the test compound, incubate the cell plates at 37° C. and 5% CO$_2$. Seven days after test compound addition, remove the plates from the incubator and add cold EtOH 96% (65 μL) to each well. After 30 minutes, remove the media and add RNase (20 μL of 50 μg/mL) (Sigma) and 1:1000 propidium iodide dilution in PBS per well. Seal the plates and incubate 1 hour at room temperature on the bench (preserved from light). Scan the plates with ACUMEN EXPLORER™ (Laser-scanning fluorescence microplate cytometer manufactured by TTP LABTECH LTD). The MCF-7 cell line grows forming aggregates, cell number as number of objects may not be able to be used as readout, so the cell number may be evaluated through estimated number of cells (calculated through the area parameter (ratio of total area of the total cells population (a designated range of peak intensity of FL-1 (PI) and the mean area of the single cells population (defined by perimeter)). Determine the IC$_{50}$ by curve fitting to a four parameter logistic for each output using GENE DATA™. The Relative IC$_{50}$ of Examples 1 and 2 in MCF7 ESR1 wild type and MCF7-ESR1 Y537N mutant cells are shown in Table 4 below. The results of this assay demonstrate anti-proliferative activity and cell growth inhibition by Examples 1 and 2 in MCF7 (ESR1 wild type) and MCF7 (ESR1 Y537N mutant) breast cancer cells. The Relative IC$_{50}$ of the exemplified compounds range from about 0.0035 to 1.176 μM in MCF7 ESR1 wild type and 0.014 to 1.86 μM in MCF7 (ESR1 Y537N mutant) breast cancer cells indicating that all exemplified compounds tested demonstrate anti-proliferative activity and cell growth inhibition in MCF7 (ESR1 wild type) and MCF7 (ESR1 Y537N mutant) breast cancer cells.

TABLE 4

Cell Proliferation Assay in MCF7 and MCF7-ESR1Y537N-682

| Example # | Relative IC$_{50}$ (μM) MCF7 ESR1 wild type | Relative IC$_{50}$ (μM) MCF7 ESR1 Y537N mutant cells |
|---|---|---|
| 1 | 0.518 ± 0.0499, n = 3 | 0.702 ± 0.389, n = 4 |
| 2 | 0.550 ± 0.238, n = 6 | 1.50 ± 0.966, n = 4 |

We claim:

1. A compound of the formula:

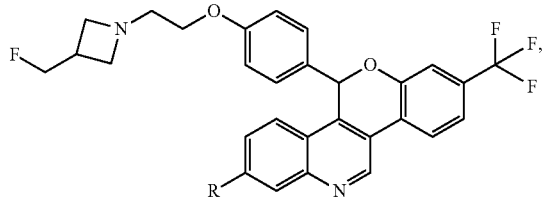

wherein R is selected from

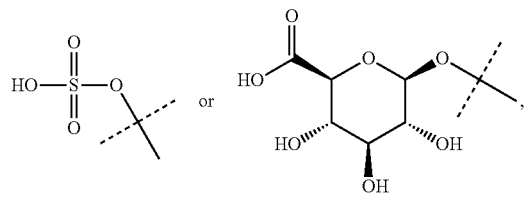

or a pharmaceutically acceptable salt thereof.

2. The compound according to claim 1, wherein the compound is

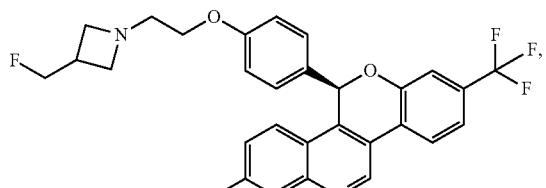

wherein R is selected from

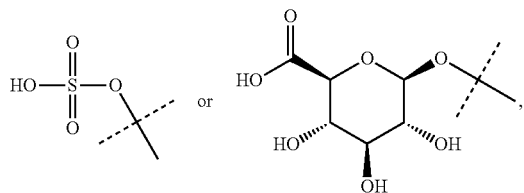

or a pharmaceutically acceptable salt thereof.

3. The compound according to claim 1, wherein the compound is

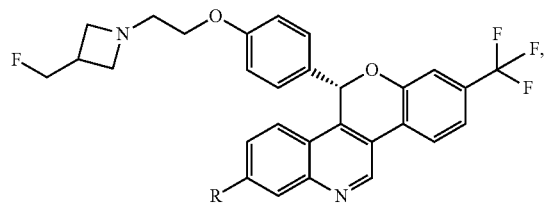

wherein R is selected from

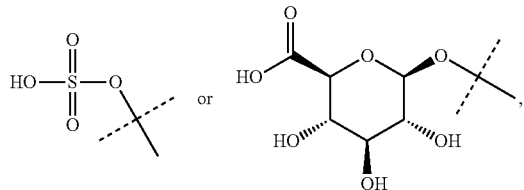

or a pharmaceutically acceptable salt thereof.

4. The compound according to claim 2, wherein the compound is

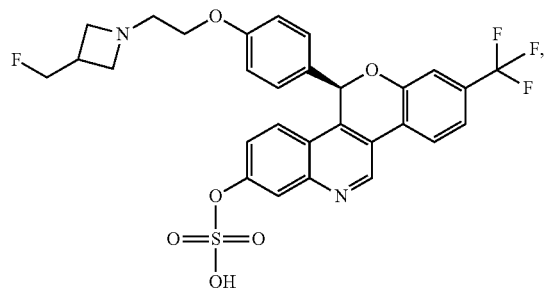 [SMILES: O=S(=O)(O)Oc1ccc2c3c(cnc2c1)-c1ccc(C(F)(F)F)cc1O[C@@H]3c1ccc(OCCN2CC(CF)C2)cc1]

or a pharmaceutically acceptable salt thereof.

5. The compound according to claim 2, wherein the compound is

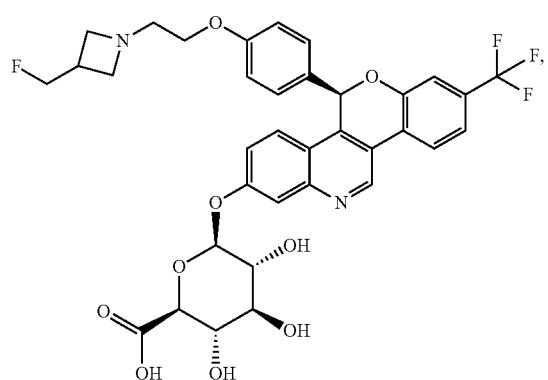 [SMILES: O=C(O)[C@H]1O[C@@H](Oc2ccc3c4c(cnc3c2)-c2ccc(C(F)(F)F)cc2O[C@@H]4c2ccc(OCCN3CC(CF)C3)cc2)[C@H](O)[C@@H](O)[C@@H]1O]

or a pharmaceutically acceptable salt thereof.

6. The compound according to claim 2, wherein the compound is

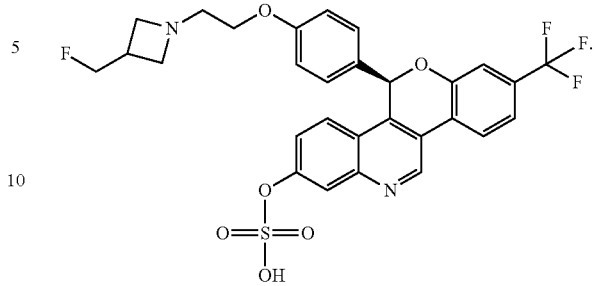

7. The compound according to claim 2, wherein the compound is

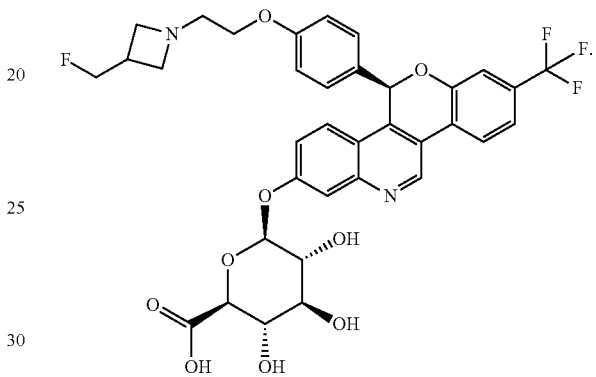

8. The compound according to claim 3, wherein the compound is

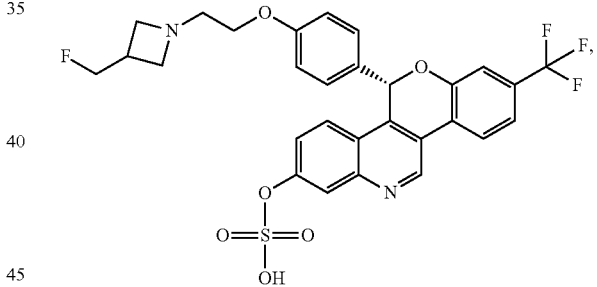

or a pharmaceutically acceptable salt thereof.

9. The compound according to claim 3, wherein the compound is

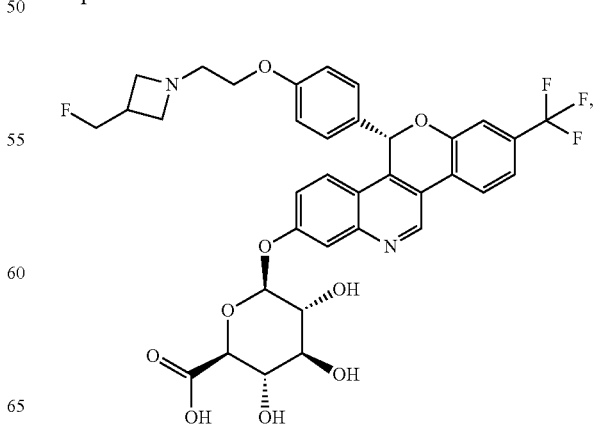

or a pharmaceutically acceptable salt thereof.

10. The compound according to claim 3, wherein the compound is

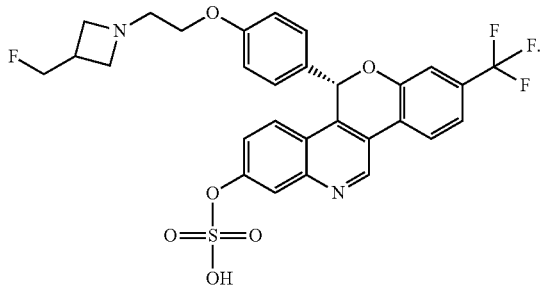 [SMILES: O=S(=O)(O)Oc1ccc2c3c(cnc2c1)-c1ccc(C(F)(F)F)cc1O[C@H]3c1ccc(OCCN2CC(CF)C2)cc1]

11. The compound according to claim 3, wherein the compound is

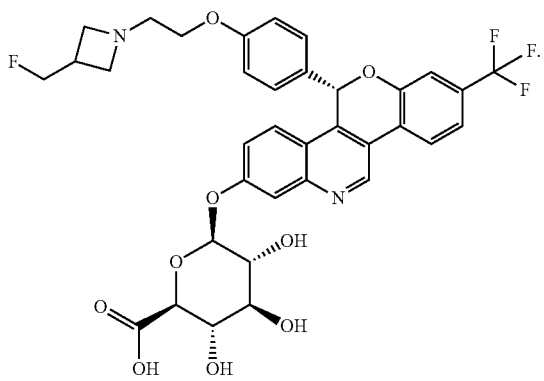 [SMILES: O=C(O)[C@H]1O[C@@H](Oc2ccc3c4c(cnc3c2)-c2ccc(C(F)(F)F)cc2O[C@H]4c2ccc(OCCN3CC(CF)C3)cc2)[C@H](O)[C@@H](O)[C@@H]1O]

12. A pharmaceutical composition comprising a compound according to claim 1, or a pharmaceutically acceptable salt thereof, with one or more pharmaceutically acceptable carriers, diluents, or excipients.

13. The pharmaceutical composition according to claim 12, comprising one or more other therapeutic agents.

14. A method of treating cancer, comprising administering to a patient in need of such treatment an effective amount of a compound according to claim 1, or a pharmaceutically acceptable salt thereof, wherein the cancer is selected from breast cancer, ovarian cancer, endometrial cancer, prostate cancer, uterine cancer, gastric cancer, and lung cancer.

15. The method according to claim 14, wherein the breast cancer is ER-positive breast cancer.

16. The method according to claim 14, wherein the gastric cancer is ER-positive gastric cancer.

17. The method according to claim 14, wherein the lung cancer is ER-positive lung cancer.

18. A method of treating cancer, comprising administering to a patient in need of such treatment an effective amount of a pharmaceutical composition according to claim 12 wherein the cancer is selected from breast cancer, ovarian cancer, endometrial cancer, prostate cancer, uterine cancer, gastric cancer, and lung cancer.

19. The method according to claim 18, wherein the breast cancer is ER-positive breast cancer.

20. The method according to claim 18, wherein the gastric cancer is ER-positive gastric cancer.

21. The method according to claim 18, wherein the lung cancer is ER-positive lung cancer.

* * * * *